(12) United States Patent
Terazaki et al.

(10) Patent No.: US 6,914,038 B2
(45) Date of Patent: Jul. 5, 2005

(54) HAIR CLEANSING COMPOSITIONS

(75) Inventors: Hiroyuki Terazaki, Tokyo (JP); Fumiko Kasuga, Tokyo (JP); Osamu Hirota, Tokyo (JP)

(73) Assignee: Kao Corporation, Tokyo (JP)

( * ) Notice: Subject to any disclaimer, the term of this patent is extended or adjusted under 35 U.S.C. 154(b) by 127 days.

(21) Appl. No.: 10/337,774

(22) Filed: Jan. 8, 2003

(65) Prior Publication Data

US 2003/0162675 A1 Aug. 28, 2003

(30) Foreign Application Priority Data

Jan. 21, 2002 (JP) .......................................... 2002-011923

(51) Int. Cl.$^7$ ............................. C11D 1/04; C11D 1/66; C11D 3/08; C11D 3/20

(52) U.S. Cl. .................... 510/122; 510/123; 510/124; 510/125; 510/126; 510/127; 510/136; 510/137; 510/158; 510/159; 510/501; 510/504; 510/506; 510/477; 510/488; 424/70.12; 424/70.22

(58) Field of Search ........................... 510/122, 123, 510/124, 125, 126, 127, 136, 137, 158, 159, 501, 504, 506, 477, 488; 424/70.12, 70.22

(56) References Cited

U.S. PATENT DOCUMENTS

| | | |
|---|---|---|
| 5,439,682 A | 8/1995 | Wivell et al. |
| 5,785,962 A | 7/1998 | Hinz et al. |
| 6,028,041 A | 2/2000 | Decoster et al. |
| 2002/0102228 A1 * | 8/2002 | Dunlop et al. ............. 424/70.1 |
| 2002/0128162 A1 * | 9/2002 | Elliott et al. ................. 510/130 |

FOREIGN PATENT DOCUMENTS

| | | |
|---|---|---|
| DE | 43 44 141 | 7/1995 |
| EP | 1 108 420 | 6/2001 |
| JP | 2001-10934 | 1/2001 |
| WO | WO 97/41827 | 11/1997 |
| WO | WO 99/36054 | 7/1999 |
| WO | WO 01/00151 | 1/2001 |
| WO | WO 03/028681 | 4/2003 |

OTHER PUBLICATIONS

U.S. Appl. No. 10/337,737, filed Jan. 8, 2003, Terazaki et al.
U.S. Appl. No. 10/337,774, filed Jan. 8, 2003, Terazaki et al.

\* cited by examiner

Primary Examiner—Gregory R. Del Cotto
(74) Attorney, Agent, or Firm—Oblon, Spivak, McClelland, Maier & Neustadt, P.C.

(57) ABSTRACT

A hair cleansing composition comprises the following ingredients (A) to (D):

(A) an anionic surfactant having a sulfate group,
(B) a cationic guar gum,
(C) an organic acid selected from a hydroxycarboxylic acid, a dicarboxylic acid or an aromatic carboxylic acid, and
(D) a salt;

and has a pH of from 1 to 4 when diluted 20-fold by weight with water.

The hair cleansing composition has good foamability and high-lubricity foam quality upon washing and smooth touch upon rinsing, and is excellent in the luster and softness of hair after drying and also superb in stability.

17 Claims, No Drawings

HAIR CLEANSING COMPOSITIONS

TECHNICAL FIELD

This invention relates to hair cleansing compositions, which have good foamability and high-lubricity foam quality upon washing and smooth touch upon rinsing, and are excellent in the luster and softness of hair after drying and also superb in stability.

BACKGROUND ART

It is a common practice to incorporate a cationic high-molecular electrolyte in a hair cleansing composition such as a shampoo so that physical properties of its foam are modified to improve touch in use during washing and to improve finger combing upon rinsing. For example, there have been proposed hair cleansing compositions containing anionic surfactants, amphoteric surfactants, cationic guar gum or nonvolatile silicones (WO 97/41827) and hair cleansing compositions containing ethoxylated organic carboxylic acid anionic surfactants, cationic derivatives of polygalactomannan gum, polysiloxane droplets, or organic carboxylic acids or salts thereof (JP-A-2001-10934). With these techniques, however, fully satisfactory performance has not been obtained yet with respect to foamability and foam lubricity upon washing and smoothness upon rinsing.

In hair treatments such as hair rinses and hair conditioners, it is also practiced to lower the pHs of their systems to impart luster and softness to hair. No attempt has, however, been made to lower the pHs of hair cleansing compositions, because the hair cleansing compositions are intended to impart neither luster nor softness in general.

With a view to providing hair cleansing compositions with such a luster and softness-imparting function as described above, the present inventors conducted research on low-pH hair cleansing compositions which made use of organic acids. A problem, however, arose in that in a low pH range, anionic surfactants as cleansing ingredients underwent decomposition, resulting in stability deteriorations such as gelling of systems and reductions in foamability.

DISCLOSURE OF THE INVENTION

The present invention has as an object the provision of a hair cleansing composition, which has good foamability and high-lubricity foam quality upon washing and smooth touch upon rinsing, and is excellent in the luster and softness of hair after drying and also superb in stability.

The present inventors have found that the decomposition of an anionic surfactant in a low pH range making use of an organic acid can be inhibited by incorporation of a salt in the system and also that a reduction in foamability due to the incorporation of a salt can be overcome by using cationic guar gum.

Described specifically, the present invention provides a hair cleansing composition comprising the following ingredients (A) to (D):

(A) an anionic surfactant having a sulfate group,
(B) a cationic guar gum,
(C) an organic acid selected from a hydroxycarboxylic acid, a dicarboxylic acid or an aromatic carboxylic acid, and
(D) a salt;

wherein the hair cleansing composition has a pH of from 1 to 4 when diluted 20-fold by weight with water.

Owing to the above-described features, the hair cleansing composition according to the present invention has good foamability and high-lubricity foam quality upon washing and smooth touch upon rinsing, and is excellent in the luster and softness of hair after drying and also superb in stability.

BEST MODES FOR CARRYING OUT THE INVENTION

Examples of the sulfate-type anionic surfactant as the ingredient (A) can include polyoxyethylene alkyl ether sulfates, polyoxyethylene alkenyl ether sulfates, alkyl sulfates, and polyoxyalkylene alkyl phenyl ether sulfates. Particularly preferred are those represented by the following formula (1) or (2):

$$R^1O(CH_2CH_2O)_mSO_3M \quad (1)$$

$$R^2OSO_3M \quad (2)$$

wherein $R^1$ represents an alkyl group or alkenyl group having 10 to 18 carbon atoms, $R^2$ represents an alkyl group having 10 to 18 carbon atoms, M represents an alkali metal, alkaline earth metal, ammonium, alkanolamine or basic amino acid, and m stands for a number of from 1 to 5.

Two or more of these sulfates may be used in combination as the ingredient (A). From the standpoint of foamability and also of liquid properties and cleansing property at the time of use, the content of the ingredient (A) may range preferably from 1 to 50 wt. %, more preferably from 8 to 30 wt. %, particularly from 10 to 22 wt. %, all based on the hair cleansing composition according to the present invention.

The content of the cationic guar gum as the ingredient (B), from the standpoint of foam lubricity and also of smoothness from washing to rinsing, may range preferably from 0.05 to 5 wt. %, more preferably from 0.1 to 3 wt. %, particularly from 0.3 to 1 wt. %, all based on the hair cleansing composition according to the present invention.

Examples of the organic acid as the ingredient (C) can include dicarboxylic acids such as malonic acid, succinic acid, glutaric acid, adipic acid, maleic acid, fumaric acid and phthalic acid; hydroxycarboxylic acids such as glycolic acid, lactic acid, hydroxyacrylic acid, oxybutyric acid, glyceric acid, malic acid, tartaric acid and citric acid; and aromatic carboxylic acids such as salicylic acid and benzoic acid. Among these, α-hydroxycarboxylic acids are preferred, with lactic acid and malic acid being particularly preferred.

Two or more of these organic acids may be used in combination as the ingredient (C). From the standpoint of improvements in the finish of hair such as luster and manageability, the content of the ingredient (C) may range preferably from 0.05 to 10 wt. %, more preferably from 0.1 to 5 wt. %, particularly from 0.5 to 1 wt. %.

The salt as the ingredient (D) may be either an inorganic salt or an organic salt. Specific examples of the inorganic salt can include sodium chloride, sodium sulfate, sodium phosphate, potassium chloride, potassium sulfate, and potassium phosphate, while specific examples of the organic salt can include trisodium citrate, sodium malate, sodium glycolate, and sodium lactate.

Two or more of these salts may be used in combination as the ingredient (D). From the standpoint of feeling in use and stability, the content of the ingredient (D) may range preferably from 0.01 to 3 wt. %, more preferably from 0.1 to 2 wt. %, particularly from 0.1 to 1 wt. %.

Incidentally, the weight ratio of the sulfate-type anionic surfactant (A) to the salt (D) may range preferably from 50/0.1 to 3/1 from the standpoint of an improvement in the stability of the ingredient (A) and also of foam volume and cleansing property.

For providing the hair cleansing composition according to the present invention with improved touch feel and also with improved luster and softness after washing, it is preferred to additionally incorporate an aromatic alcohol. Examples of the aromatic alcohol can include benzyl alcohol, benzyloxyethanol, with benzyl alcohol and benzyloxyethanol being particularly preferred.

Two or more aromatic alcohols may be used in combination. The content of the aromatic alcohol may range preferably from 0.01 to 20 wt. %, more preferably from 0.1 to 10 wt. %, particularly form 0.5 to 5 wt. %, all based on the hair cleansing composition according to the present invention.

To further improve the foamability of the hair cleansing composition according to the present invention, one or more surfactants other than the ingredient (A), said surfactants being selected from anionic surfactants, nonionic surfactants and amphoteric surfactants, may also be incorporated.

The anionic surfactants other than the ingredient (A) can include sulfonate-type anionic surfactants and carboxylate-type anionic surfactants. Illustrative are alkyl sulfosuccinate salts, alkyl polyoxyalkylene sulfosuccinate salts, higher fatty acid salts, and alkanesulfonate salts.

Examples of the nonionic surfactants can include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, and alkyl glycosides. Among these, alkyl glycosides, polyoxyalkylene ($C_8$–$C_{20}$) fatty acid esters, polyoxyethylene sorbitan fatty acid esters, polyoxyethylene hydrogenated castor oil and fatty acid alkanolamides are preferred. Preferred fatty acid alkanolamides are those containing acyl groups having the carbon numbers of from 8 to 18, especially from 10 to 16. The fatty acid alkanolamides can be either monoalkanolamides or dialkanolamides. Preferred are those containing hydroxyalkyl groups having the carbon numbers of from 2 to 3. Illustrative are oleic diethanolamide, palm kernel oil fatty acid diethanolamide, coconut oil fatty acid diethanolamide, lauric diethanolamide, polyoxyethylene coconut oil fatty acid monoethanolamides, coconut oil fatty acid monoethanolamides, lauric isopropanolamide, and lauric monoethanolamide.

The amphoteric surfactants can include betaine-type surfactants. Among these, betaine-type surfactants such as alkyldimethylaminoacetic acid betaines and fatty acid amidopropyl betaines are more preferred, with fatty acid amidopropyl betaines being particularly preferred. Of these fatty acid amidopropyl betaines, preferred are those having acyl groups whose carbon numbers are from 8 to 18, especially from 10 to 16. Particularly preferred are lauramidopropyl betaine, palm kernel oil fatty acid amidopropyl betaines, and coconut oil fatty acid amidopropyl betaines.

These surfactants other than the ingredient (A) can be incorporated, as needed, in the hair cleansing composition according to the present invention. When the hair cleansing composition according to the present invention is formulated into the form of an aqueous liquid cleansing composition, use of a fatty acid amidopropyl betaine or fatty acid alkanolamide in combination with the ingredient (A) is particularly preferred because this makes it possible not only to further improve the foaming power but also to obtain adequate liquid properties.

When a fatty acid amidopropyl betaine or fatty acid alkanolamide is incorporated as described above, its content may range preferably from 0.1 to 10 wt. %, more preferably from 1 to 8 wt. %, particularly from 2 to 6 wt. %, all based on the hair cleansing composition according to the present invention, since good foam-boosting effect can be obtained.

In the hair cleansing composition according to the present invention, a silicone can be incorporated to improve the post-drying finish. Examples of the silicone can include the followings:

(1) Dimethylpolysiloxanes

Illustrative are those represented by the following formula:

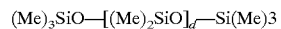

$(Me)_3SiO-[(Me)_2SiO]_d-Si(Me)_3$ wherein each Me represents a methyl group, and d stands for a number of from 3 to 20,000.

(2) Amino-Modified Silicones

One having an average molecular weight of from about 3,000 to 100,000 and listed under the name of "Amodimethicone" in the third edition of the CTFA dictionary (Cosmetic Ingredient Dictionary, U.S.A.) is preferred, although a variety of amino-modified silicones are usable. This amino-modified silicone can be used preferably as an aqueous emulsion, and its commercial products include "SM 8704C" (Dow Corning Toray Silicone Co., Ltd.) and "DC 929" (Dow Corning Corporation).

(3) Other Silicones

As silicones other than those described above, there are also polyether-modified silicones, methylphenylpolysiloxane, fatty-acid-modified silicones, alcohol-modified silicones, alkoxy-modified silicones, epoxy-modified silicones, fluorine-modified silicones, cyclic silicones, alkyl-modified silicones, and the like.

Two or more of these silicones may be used in combination. The content of the silicone may range preferably from 0.01 to 20 wt. %, more preferably from 0.1 to 10 wt. %, particularly from 1 to 5 wt. %, all based on the hair cleansing composition according to the present invention.

To provide the hair cleansing composition according to the present invention with improved stability, foam lubricity and finish, a higher alcohol may also be incorporated. Preferred higher alcohols are those containing linear or branched, particularly linear alkyl groups having the carbon numbers of from 12 to 22, especially from 12 to 16. Specific examples can include lauryl alcohol, myristyl alcohol and cetyl alcohol, with myristyl alcohol being particularly preferred.

Two or more higher alcohols may be used in combination. The content of the higher alcohol may range preferably from 0.05 to 5 wt. %, more preferably from 0.1 to 3 wt. %, particularly from 0.5 to 2 wt. %, all based on the hair cleansing composition according to the present invention.

In addition to the above-described ingredients, ingredients which are employed in ordinary hair cleansing compositions can also be incorporated in the hair cleansing composition according to the present invention as needed depending upon the purpose of use. Such ingredients can include, for example, antidandruff agents; vitamins; anti-inflammatories; chelating agents; humectants such as propylene glycol, glycerin, diethylene glycol monoethyl ether, sorbitol and panthenol; colorants such as dyes and pigments; viscosity controlling agents such as hydroxyethylcellulose, methylcellulose, polyethylene glycol, ethanol, and clay mineral; pH adjusters such as potassium hydroxide; plant extracts; pearlants; fragrances; color additives; ultraviolet absorbers; antioxidants; and ingredients described in ENCYCLOPEDIA OF SHAMPOO INGREDIENTS (MICELLE PRESS).

From the viewpoint of imparting luster and softness to hair and also reducing irritation, the hair cleansing composition according to the present invention has a pH of from 1 to 4, preferably from 2 to 4, particularly from 3 to 4 when diluted 20-fold by weight with water (to the concentration upon application to hair).

The form of the hair cleansing composition according to the present invention can be chosen as desired, including a liquid form, a powder form, a gel form, and a granular form. However, a liquid form making use of water or a lower alcohol as a solvent, especially water is preferred.

The hair cleansing composition according to the present invention can be formulated into one for use in a bathroom a shampoo composition, a shampoo with rinse, a treatment or a conditioner, especially a shampoo composition.

EXAMPLES

In the following Examples and Comparative Examples, each "pH" indicates a pH as measured when diluted 20-fold by weight with water.

Examples 1–4 and Comparative Examples 1–4

Shampoo compositions shown in Table 1 were prepared, and their organoleptic ranking was conducted.

Washing Method

Subsequent to thorough moistening of hair, 5 g or 10 g (5 g for semi-long hair, 10 g for long hair) of a shampoo composition were dispensed, and then, the hair was washed. The hair was rinsed thoroughly and then dried fully with hot air from a dryer.

(Organoleptic Ranking)

Ranking was conducted by five expert panelists in accordance with the following ranking systems, and based on average scores, the shampoo compositions were ranked.

Ranking systems (1) Foam volume upon foaming
4: Foams very well.
3: Foams well.
2: Foams to ordinary level.
1: Does not foam well.
0: Does not foam.
(2) Lubricity of foam
4: Foams have very high lubricity.
3: Foams have good lubricity.
2: Foams have some lubricity.

1: Foams do not have much lubricity.
0: Foams have not lubricity.
(3) Fineness of foams
4: Foams are very fine.
3: Foams are fine.
2: Foams are rather fine.
1: Foams are rather coarse.
0: Foams are coarse.
(4) Smoothness upon rinsing
4: Very smooth.
3: Smooth.
2: Slightly smooth.
1: Not smooth.
0: Not smooth at all.
(5) Softness of hair after drying
4: Very soft.
3: Soft.
2: Slightly soft.
1: Not soft.
0: Not soft at all.
(6) Luster of hair after drying
4: Pronounced improvement in luster is observed.
3: Improvement in luster is observed.
2: Some improvement in luster is observed.
1: No improvement in luster.
0: Luster is lost.

(Ranking)

A: Average ranking score $\geq 3.5$
B: 3.5>Average ranking score $\geq 2.5$
C: 2.5>Average ranking score $\geq 1.5$
D: 1.5>Average ranking score (Stability)

A shelf stability test was conducted at 50° C. for 1 month, and ranking was performed in accordance with the following system.

A: Neither properties nor use feeling remained unchanged.
B: Properties remained unchanged, but changes occurred in use feeling (deteriorations in foam volume, foam lubricity and the like).
C: Properties and use feeling were both changed [separation; changes in liquid properties (gelation, viscosity drop); foam volume, foam smoothness and the like were deteriorated].

TABLE 1

|  |  | \multicolumn{4}{c}{Examples} | \multicolumn{4}{c}{Comparative Examples} |
|---|---|---|---|---|---|---|---|---|---|
|  |  | 1 | 2 | 3 | 4 | 1 | 2 | 3 | 4 |
| Ingredients (wt. %) | | | | | | | | | |
| (A) | Sodium POE(2) lauryl ether sulfate | 10 | 15 | 10 | 10 | — | 15 | 10 | 10 |
|  | Sodium lauryl sulfate | 5 | — | 5 | — | — | — | 5 | — |
| (B) | Cationic guar gum | 0.3 | 0.5 | 0.3 | 0.4 | 0.3 | 0.5 | — | — |
| (C) | Glycolic acid | — | 0.5 | — | — | — | 0.5 | — | — |
|  | Malic acid | 0.75 | — | — | 0.7 | 0.75 | — | — | 0.05 |
|  | Lactic acid | 0.1 | — | 1 | — | 0.1 | — | 1 | — |
| (D) | Sodium chloride | 0.5 | 1 | — | 0.5 | 0.5 | — | — | — |
|  | Trisodium citrate | — | — | 1 | — | — | — | 1 | — |
| Others | Benzyl alcohol | 0.1 | 0.1 | 0.1 | 0.1 | 0.1 | — | — | — |
|  | Lauramidopropyl betaine | — | — | — | 2 | 8 | — | — | 2 |
|  | Cocoyl monoethanolamide | — | — | 1 | — | 1 | — | 1 | — |
|  | Cationic cellulose | 0.3 | — | — | — | 0.3 | — | 0.3 | 0.3 |
|  | Purified water | Bal. | Bal. | Bal. | Bal. | Bal. | Bal. | Bal. | Bal. |
| pH (when diluted 20-fold by weight) | | 3.4 | 4 | 3.9 | 3.5 | 3.4 | 4 | 3.9 | 5.3 |
| Ranking | | | | | | | | | |
| Foam volume | | A | B | A | A | D | A | B | C |
| Foam lubricity | | A | B | A | A | C | C | B | C |
| Smoothness upon rinsing | | A | A | A | A | C | C | C | B |
| Hair softness after drying | | A | A | A | A | B | C | C | C |
| Hair luster after drying | | A | B | B | A | B | C | C | C |
| Stability | | A | A | A | A | A | C | C | B |

Example 5
Clear Shampoo

|  | (wt. %) |
|---|---|
| Sodium POE (2) lauryl ether sulfate | 10.0 |
| Cationic guar gum | 0.1 |
| Malic acid | 0.7 |
| Sodium chloride | 1.0 |
| Lauramidopropyl betaine | 1.0 |
| Cocoyl monoethanolamide | 0.3 |
| Glycerin | 1.0 |
| Sodium hydroxide | q.s. to pH 4 |
| Deionized water | Balance |

The above-described shampoo was excellent in foam volume and foam lubricity upon washing, smoothness upon rinsing, and hair luster and softness after drying, and was also superb in stability.

Example 6
Conditioning Shampoo

|  | (wt. %) |
|---|---|
| Sodium POE (2) lauryl ether sulfate | 8.0 |
| Cationic guar gum | 0.5 |
| Lactic acid | 1.5 |
| Trisodium citrate | 1.0 |
| Lauramidopropyl betaine | 3.0 |
| Cocoyl monoethanolamide | 0.7 |
| Myristyl alcohol | 1.0 |
| Ethylene glycol distearate | 3.0 |
| Glycerin | 1.0 |
| Deionized water | Balance |

The above-described shampoo (pH 3.5) was excellent in foam volume and foam lubricity upon washing, smoothness upon rinsing, and hair luster and softness after drying, and was also superb in stability.

Example 7
Conditioning Shampoo

|  | (wt. %) |
|---|---|
| Sodium POE (2) lauryl ether sulfate | 11.0 |
| Sodium lauryl sulfate | 5.0 |
| Cationic guar gum | 0.3 |
| Malic acid | 0.75 |
| Lactic acid | 0.1 |
| Sodium chloride | 0.2 |
| Benzyl alcohol | 0.5 |
| Cocoyl monoethanolamide | 1.0 |
| Dimethicone (polymerization degree: 2,000) | 0.25 |
| Dimethicone (polymerization degree: 200) | 0.25 |
| Amodimethicone | 0.1 |
| Myristyl alcohol | 1.0 |
| Cetanol | 0.5 |
| Ethylene glycol distearate | 3.0 |
| Cationic hydroxyethylcellulose | 0.3 |
| Glycerin | 1.0 |
| Sodium hydroxide | q.s. to pH 3.7 |
| Deionized water | Balance |

The above-described shampoo was excellent in foam volume and foam lubricity upon washing, smoothness upon rinsing, and hair luster and softness after drying, and was also superb in stability.

Example 8
Conditioning Shampoo

|  | (wt. %) |
|---|---|
| Sodium POE (2) lauryl ether sulfate | 8.0 |
| Cationic guar gum | 0.3 |
| Malic acid | 0.5 |
| Lactic acid | 0.5 |
| Sodium chloride | 1.0 |
| Lauramidopropyl betaine | 3.0 |

-continued

|  | (wt. %) |
|---|---|
| Myristyl alcohol | 1.0 |
| Cetanol | 0.5 |
| Behenyltrimonium chloride | 0.5 |
| Ethylene glycol distearate | 2.0 |
| Sodium hydroxide | q.s. to pH 3.9 |
| Deionized water | Balance |

The above-described shampoo was excellent in foam volume and foam lubricity upon washing, smoothness upon rinsing, and hair luster and softness after drying, and was also superb in stability.

Example 9

Antidandruff Shampoo

|  | (wt. %) |
|---|---|
| Sodium POE (2) lauryl ether sulfate | 10.0 |
| Sodium lauryl sulfate | 5.5 |
| Cationic guar gum | 0.3 |
| Malic acid | 1.0 |
| Sodium chloride | 0.2 |
| Benzyloxyethanol | 0.5 |
| Cocoyl monoethanolamide | 0.5 |
| Dimethicone (polymerization degree: 2,000) | 0.5 |
| Dimethicone (polymerization degree: 200) | 0.5 |
| Myristyl alcohol | 1.0 |
| Cetanol | 0.5 |
| Ethylene glycol distearate | 3.0 |
| Cocoyl benzalconium chloride | 0.5 |
| Cationic hydroxyethylcellulose | 0.3 |
| Glycerin | 1.0 |
| Sodium hydroxide | q.s. to pH 4 |
| Deionized water | Balance |

The above-described shampoo was excellent in foam volume and foam lubricity upon washing, smoothness upon rinsing, and hair luster and softness after drying, and was also superb in stability.

What is claimed is:

1. A hair cleansing composition comprising the following ingredients (A) to (D):
   (A) an anionic surfactant having a sulfate group,
   (B) a cationic guar gum,
   (C) an organic acid selected from a hydroxycarboxylic acid, a dicarboxylic acid or an aromatic carboxylic acid, and
   (D) a salt;
wherein said hair cleansing composition has a pH of from 1 to 4 when diluted 20-fold by weight with water.

2. A hair cleansing composition according to claim 1, wherein a content ratio by weight of said ingredient (A) to said ingredient (D) is from 50/0.1 to 3/1.

3. A hair cleansing composition according to claim 1 or 2, further comprising an aromatic alcohol.

4. A hair cleansing composition according to claim 1 or 2, further comprising a fatty acid amidopropyl betaine or a fatty acid alkanolamide.

5. A hair cleansing composition according to claim 1 or 2, further comprising a silicone.

6. A hair cleansing composition according to claim 1, further comprising two or more aromatic alcohols.

7. A hair cleansing composition according to claim 1, further comprising from 0.01 to 20 wt % of two or more aromatic alcohols; wherein said wt % is based on the hair cleansing composition.

8. A hair cleansing composition according to claim 1, further comprising from 0.1 to 10 wt % of two or more aromatic alcohols; wherein said wt % is based on the hair cleansing composition.

9. A hair cleansing composition according to claim 1, further comprising two or more silicones.

10. A hair cleansing composition according to claim 1, further comprising from 0.01 to 20 wt % of two or more silicones; wherein said wt % is based on the hair cleansing composition.

11. A hair cleansing composition according to claim 1, further comprising from 0.1 to 10 wt % of two or more silicones; wherein said wt % is based on the hair cleansing composition.

12. A hair cleansing composition according to claim 1, further comprising a higher alcohol.

13. A hair cleansing composition according to claim 1, further comprising two or more higher alcohols.

14. A hair cleansing composition according to claim 1, further comprising from 0.05 to 5 wt % of two or more higher alcohols; wherein said wt % is based on the hair cleansing composition.

15. A hair cleansing composition according to claim 1, wherein said hair cleansing composition has a pH of from 2 to 4 when diluted 20-fold by weight with water.

16. A hair cleansing composition according to claim 1, wherein said hair cleansing composition has a pH of from 3 to 4 when diluted 20-fold by weight with water.

17. A method, which comprises:
    applying the hair cleansing composition according to claim 1 to keratin fibers; and
    rinsing the keratin fibers with water.

* * * * *